United States Patent
Shahi et al.

(10) Patent No.: US 11,226,342 B2
(45) Date of Patent: Jan. 18, 2022

(54) METHODS UTILIZING D-DIMER FOR DIAGNOSIS OF PERIPROSTHETIC JOINT INFECTION

(71) Applicant: ROWAN UNIVERSITY, Glassboro, NJ (US)

(72) Inventors: Alisina Shahi, Stratford, NJ (US); Javad Parvizi, Philadelphia, PA (US)

(73) Assignee: Rowan University, Glassboro, NJ (US)

( * ) Notice: Subject to any disclaimer, the term of this patent is extended or adjusted under 35 U.S.C. 154(b) by 404 days.

(21) Appl. No.: 16/080,416

(22) PCT Filed: Mar. 1, 2017

(86) PCT No.: PCT/US2017/020240
§ 371 (c)(1),
(2) Date: Aug. 28, 2018

(87) PCT Pub. No.: WO2017/151794
PCT Pub. Date: Sep. 8, 2017

(65) Prior Publication Data
US 2020/0225246 A1 Jul. 16, 2020

Related U.S. Application Data

(60) Provisional application No. 62/301,664, filed on Mar. 1, 2016.

(51) Int. Cl.
*G01N 33/00* (2006.01)
*G01N 33/68* (2006.01)

(52) U.S. Cl.
CPC . *G01N 33/6893* (2013.01); *G01N 2333/4737* (2013.01); *G01N 2800/26* (2013.01); *G01N 2800/52* (2013.01)

(58) Field of Classification Search
CPC ....... G01N 33/6893; G01N 2333/4737; G01N 2800/26; G01N 2800/52
See application file for complete search history.

(56) References Cited

U.S. PATENT DOCUMENTS

2008/0183062 A1   7/2008   Hazui et al.
2009/0305301 A1   12/2009  Mirshahi et al.

FOREIGN PATENT DOCUMENTS

WO   2010036930 A1   4/2010
WO   2013112216 A1   8/2013
WO   2015164188 A1   10/2015

OTHER PUBLICATIONS

Kovacs, Michael J. et al. "A comparison of three rapid D-dimer methods for the diagnosis of venous thromboembolism." British J. Hematology (2001) 115 140-144. (Year: 2001).*
Lippi, Giuseppe et al. "Causes of elevated d-dimer in patients admitted to a large urban emergency department." European Journal of Medicine (2014) 25 45-48. (Year: 2014).*
Zimmerli, W. "Clinical presentation and treatment of orthopaedic implant-associated infection." Journal of Internal Medicine (2014) 276 111-119. (Year: 2014).*
Ellenrieder, et al., Two-stage revision of implant-associated infections with total hip and knee arthroplasty, GMS Krankenhaushygiene Interdisziplinar, vol. 6, No. 1 ,2011 ,pp. 1-8.
Rodelo, Jr., et al., D-dimer is a significant prognostic factor in patients with suspected infection and sepsis, Am J Emerg Med, vol. 30, No. 9 ,Nov. 2012 ,pp. 1991-1999.
International Search Report and Written Opinion for PCT International Application No. PCT/US2017/020240 filed Mar. 1, 2017.

* cited by examiner

*Primary Examiner* — Christopher Adam Hixson
(74) *Attorney, Agent, or Firm* — Saul Ewing Arnstein & Lehr LLP; Domingos J. Silva

(57) ABSTRACT

This invention relates to the detection and quantification of D-dimer levels in a sample derived from a patient having or suspected of having periprosthetic joint infection (PJI) and subsequent diagnosis of PJI.

11 Claims, 6 Drawing Sheets

METHODS UTILIZING D-DIMER FOR DIAGNOSIS OF PERIPROSTHETIC JOINT INFECTION

CROSS REFERENCE TO RELATED APPLICATIONS

This application is a 35 U.S.C. § 371 national phase application of, and claims priority to, International Application No. PCT/US2017/020240, filed Mar. 1, 2017, which claims the benefit of priority under 35 U.S.C. 119(e) to U.S. Provisional Application No. 62/301,664, filed Mar. 1, 2016, the contents of which are incorporated herein by reference in their entireties.

FIELD OF THE INVENTION

This invention relates to the detection and quantification of D-dimer levels in a sample derived from a patient having or suspected of having periprosthetic joint infection.

BACKGROUND OF THE INVENTION

Despite its immense impact on patients and the society, the diagnosis of periprosthetic joint infection (PJI) remains imperfect and often very challenging. There is no "gold standard" for diagnosis of PJI, Recent studies have demonstrated that synovial biomarkers, such as serum C-reactive protein (CRP) (mg/dL) levels have a promising role in the diagnosis of PJI with excellent accuracy. Other standard laboratory tests include erythrocyte sedimentation rate (ESR) and synovial fluid leukocyte count and differential, which were not developed specifically for the diagnosis of PJI. However, there are many disadvantages to the use of synovial markers for diagnosis of PJI as obtaining the synovial fluid is invasive, carries the potential for introducing infection into the joint, and not infrequently there is an issue with obtaining adequate fluid from the joint for analysis. Although a number of serum biomarkers may have been evaluated in the past for their use in diagnosing PJI, the wide variation in their level of thresholds, as well as, other factors such as age, gender and the presence or absence of inflammatory conditions complicate the diagnostic interpretation of the value associated to these biomarkers. There is a dire need for a more accurate serum biomarkers for diagnosing PJI more accurately and assist practicing orthopedic surgeons to effectively treat and improve patient outcomes among those who are suffering or are at risk of developing PJI.

SUMMARY OF THE INVENTION

In some embodiments, the invention is directed to a method for diagnosing joint infections, preferably periprosthetic joint infection (PJI), in a patient. In at least one embodiment, the invention is directed to methods of detecting PJI from in a patient who has undergone surgical bone implant or repair. In another embodiment, the invention is directed to methods of detecting biomarkers associated with such infections particularly PJI.

In some embodiments, the method provides for steps of (a) obtaining a sample from a patient in need of detection, wherein the sample contains D-dimer; (b) quantifying the level of D-dimer present in the sample; and (c) diagnosing the patient as having PJI, wherein a D-dimer level greater than 300, 400, 800 or 850 ng/mL in the sample indicates that the patient as having PJI. In further embodiments, the quantifying step is performed by an immunoassay. In yet further embodiments the sample is one of a plasma sample, blood sample, sputum sample, lavage, synovial fluid, or combinations thereof.

In another embodiment, the present invention provides a method of screening for infection in a joint of a patient, said method comprising the steps of (a) extracting a serum sample such as plasma, blood, or any combinations thereof, (b) applying the sample to a detector device employing detection reagents which are specific for D-dimer markers, wherein said detection reagents are adapted to detect a threshold level of D-dimer level correlated with a presence of infection; (c) ascertaining the threshold levels of the D-dimer in said sample, wherein if the concentration D-dimer is above 300, 400, 800, 850, 1100, 1200 ng/mL, it indicates a positive screen for infection of the joint. In another embodiment, at least another secondary biomarkers may be employed to increase sensitivity of the diagnosis.

In another embodiment, the present invention may further include therapeutic steps to alleviate the infection once a positive screen for infection of the joint is determined. In some embodiments, the invention is directed to a method for determining whether or not a patient who has undergone spacer insertion should undergo re-implantation. In some embodiments, the method provides for steps of (a) obtaining a serum sample comprising D-dimer from the patient; (b) quantifying the level of D-dimer present in the sample; and (c) determining whether or not to proceed with re-implantation, wherein a D-dimer threshold level greater than 400 or 850 ng/mL in the sample is indicative of additional risk and poor prognosis. In another embodiment, threshold level greater than 300, 400, 800, 850, 1100, 1200 ng/ml indicates to not proceed with re-implantation, while a D-dimer level lower than 400, 800, 850, 1100 ng/mL in the sample indicates good prognosis and is affirmative indication to proceed with re-implantation.

In other embodiments, a D-dimer level greater than 300 ng/mL in the sample indicates to not proceed with re-implantation, and a D-dimer level lower than 300 ng/mL in the sample indicates to proceed with re-implantation. In yet other embodiments, a D-dimer level greater than 200 ng/mL in the sample indicates to not proceed with re-implantation, and a D-dimer level lower than 200 ng/mL in the sample indicates to proceed with re-implantation. In further embodiments, the quantifying step is performed by an immunoassay. In yet further embodiments, the sample is one of a plasma sample, blood sample, sputum sample, lavage, synovial fluid, or combinations thereof. In another embodiment, kits for practicing the disclosed methodologies are described.

DETAILED DESCRIPTION OF THE INVENTION

Periprosthetic joint infection (PJI) is one of the most dreaded complications after total joint arthroplasty, yet diagnosis is far from perfect. Historically, a positive diagnosis of PJI is made when one of two major criteria exists or three out of five minor criteria exist. The major criteria include 1) two positive periprosthetic cultures with phenotypically identical organisms, or 2) a sinus tract communicating with the joint. The minor criteria include 1) elevated serum C-reactive protein levels (CRP) and elevated erythrocyte sedimentation rate (ESR), 2) elevated synovial fluid white blood cell (WBC) count or positive change on a leukocyte esterase test strip, 3) elevated synovial fluid polymorphonuclear neutrophil percentage (PMN %), 4) positive histological analysis of periprosthetic tissue, and 5) a single positive culture. (Musculoskeletal Infection Society, MSIS criteria).

The major criteria for diagnosing PJI suffer from several limitations. Taking periprosthetic cultures are invasive and involve drawing samples directly from the affected joint. Furthermore, at least two positive cultures are necessary to satisfy a diagnosis of PJI. The minor criteria suffer from similar limitations. Elevated CRP levels are known to signify a wide number of inflammatory conditions or disorders and as such are relatively not specific for PJI, which is why it is rendered minor criteria. The same issue exists for ESR, which is utilized for diagnosing a number of diseases other than PJI (e.g. multiple myeloma, arteritis, various autoimmune diseases, lupus), and as such is relatively not specific for PJI. Furthermore, the elevated synovial white blood count, neutrophil percentages, and especially histological analysis of periprosthetic tissue are likewise invasive and carry additional risks and burdens to the patient.

Figure 1:
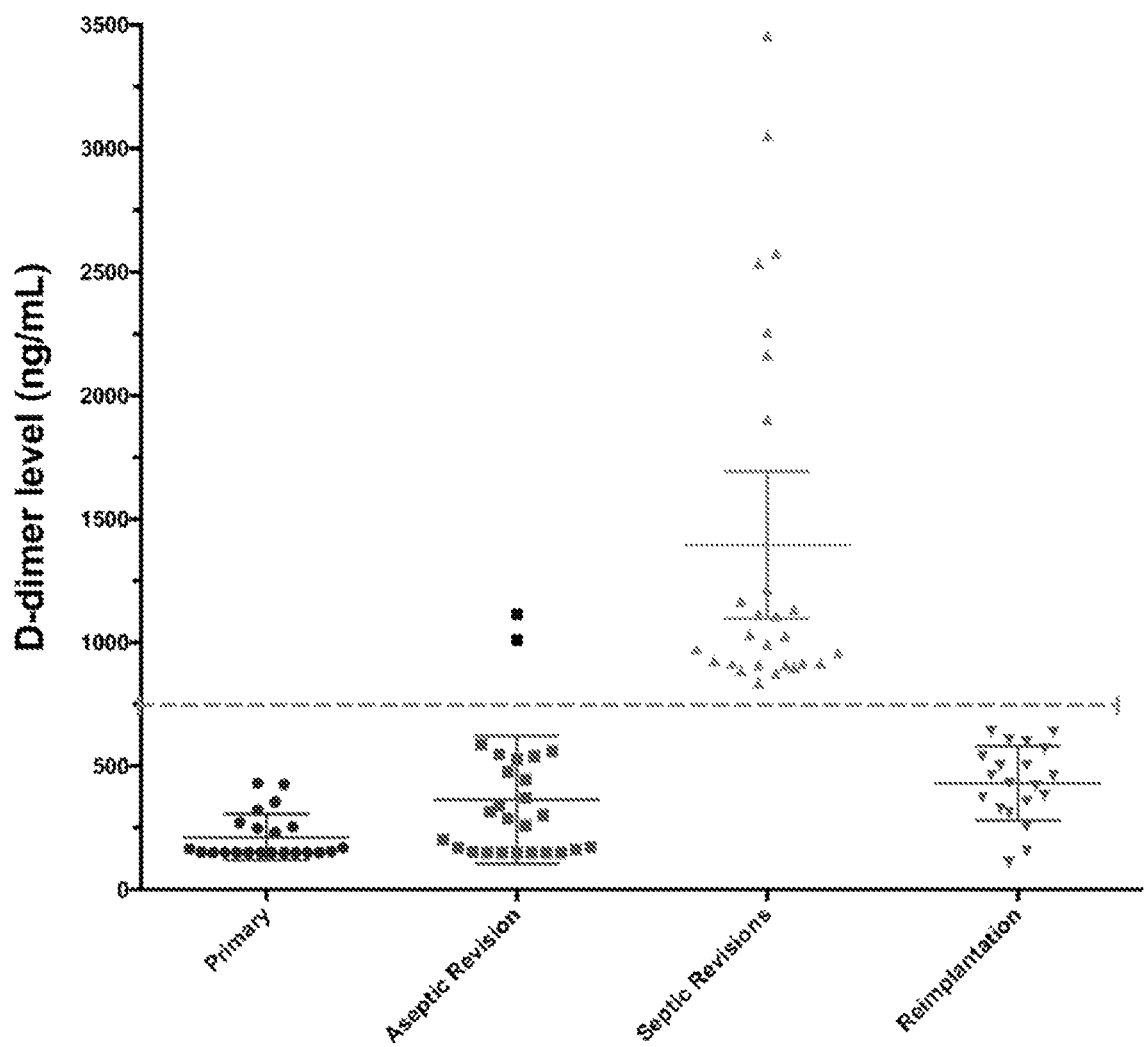
FIG. 1 displays D-dimer levels in the patient study groups of Example 2.

The present invention overcomes these limitations by providing, in one embodiment, a method of detecting serum D-dimer levels in a sample obtained from the patient, e.g. a plasma, blood, urine, sputum, lavage, or synovial fluid sample, wherein elevated D-dimer levels identify a patient as suffering or at risk of having PJI. In some embodiments, elevated serum D-dimer level forms the basis for a positive diagnosis of PJI. Such diagnostic methods are highly sensitive [FIG. 1] and represent a significant improvement over the existing major and minor criteria for diagnosing PJI. Because the diagnostic methods are capable of detecting circulating D-dimer levels, such as those circulating in the bloodstream, the such methods are non-invasive and do not carry the potential risks involved in biopsies or other methods that rely on taking synovial samples, thus presenting an immediate improvement over the major criteria and a number of the minor criteria. Although measuring CRP and ESR is non-invasive, because elevated CRP and/or elevated ESR are indicative of a large spectrum of pathologies and/or disorders, D-dimer represents a significant improvement over both.

Elevated D-dimer levels are indicative of relatively few pathological conditions, such as thrombosis. This is because D-dimers are protein products of cross-linked fibrin degradation (fibrin degradation product, or FDP) that are present in the blood of most healthy individuals in only negligible amounts, of the order about 100 ng/mL to about 200 ng/mL.

In fibrinolysis, a fibrin clot is broken down by the enzyme plasmin; plasmin cuts the fibrin clot at various places, leading to the production of circulating fragments that are eventually degraded further by proteases and other enzymes by the kidney and/or liver.

As objective evidence of increased fibrinolysis, elevated blood concentration of D-dimer is by extension evidence of intravascular coagulation and thrombotic disease. The D-dimer test is now routinely used in the first-line assessment of patients suspected of suffering venous thromboembolism (VTE), which can present as either deep vein thrombosis (DVT) or pulmonary embolism (PE). Although elevation of D-dimer levels is invariably evident in those with VTE, not until the present disclosure has the use of D-dimer has ever been associated to the ongoing or risk of developing bone infection. Through the present invention that, surprisingly, elevated D-dimer levels is a sensitive, evidence for detecting PJI.

In fact, it has been discovered that the correlation between elevated D-dimer levels and PJI is so strong that absence of an elevated D-dimer levels, or rather normal D-dimer levels, those of ordinary skill in the art can rule out PJI as a potential pathology. Thus, one embodiment of the present invention relates to the detection and quantification of D-dimer levels in a sample derived from a patient having or suspected of having periprosthetic joint infection.

Elevated D-dimer levels may be defined as any D-dimer levels that are significantly above those D-dimer levels found circulating in the blood of healthy individuals. For example, D-dimer is present in the order from about 100 ng/mL to about 200 ng/mL in the majority of healthy individuals, although such healthy individuals may have D-dimer levels up to about 300 ng/mL or about 400 ng/mL without any pathological conditions, or as low as 25 ng/mL, e.g. about 25 ng/mL to about 400 ng/mL and any intervening ranges, below 400 ng/mL, below 350 ng/mL, below 300 ng/mL, below 250 ng/mL, below 200 ng/mL below 150 ng/mL, below 100 ng/mL, and below 50 ng/mL, and any intervening ranges. Therefore, D-dimer levels in amounts above 400 ng/mL, especially those levels above 800 or 850 ng/mL, may be considered elevated, and thus may serve as the basis for a diagnosis of PJI. As described herein, D-dimer levels from about 400 ng/mL to about 5000 ng/mL along with any intervening ranges may be considered elevated and thus indicative of PJI. The D-dimer level may be, for example, above 400 ng/mL, above 450 ng/mL, above 500 ng/mL, above 550 ng/mL, above 600 ng/mL, above 650 ng/mL, above 700 ng/mL, above 750 ng/mL, above 800 ng/mL, above 850 ng/mL, above 900 ng/mL, above 950 ng/mL, above 1000 ng/mL, above 1050 ng/mL, above 1100 ng/mL, above 1150 ng/mL, above 1200 ng/mL, above 1250 ng/mL, above 1300 ng/mL, above 1350 ng/mL, above 1400 ng/mL, above 1450 ng/mL, above 1500 ng/mL, above 1600 ng/mL, above 1700 ng/mL, above 1800 ng/mL, above 1900 ng/mL, above 2000 ng/mL, above 2500 ng/mL, above 3000 ng/mL, above 3500 ng/mL, above 4000 ng/mL, above 4500 ng/mL, above 5000 ng/mL, and any intervening ranges. This diagnosis of PJI may be made with or without additional criteria, i.e. elevated D-dimer levels may be considered a major diagnostic criterion, or elevated D-dimer levels may be considered a minor diagnostic criterion. As a major diagnostic criterion, elevated D-dimer levels may be the sole basis for a positive diagnosis of PJI.

Just as elevated D-dimer levels may serve as the basis for a diagnosis of PJI, normal D-dimer levels (as defined herein) may serve as the basis for eliminating PJI as a potential pathology. This has several fundamental implications in the treatment and management of PJI. The standard treatment for PJI, once a positive diagnosis of PJI is made, is to surgically remove the prosthetic implant, insert an antibiotic-impregnated spacer, e.g. a cement spacer ("spacer implantation"), and monitor the joint/surrounding tissue for signs of infection. Once it appears that the infection has subsided, the spacer is removed and a new implant is inserted into the patient ("re-implantation"). As can be seen, this is a highly invasive procedure requiring multiple surgeries, each with their own potential complications and infections, and several potential biopsies. Furthermore, the failure rate of re-implantation is high, with as many as up to 30% re-implantations resulting in subsequent PJI. This may be due to many reasons, for example failing to properly eliminate the PJI prior to re-implantation, but in each instance, the highly invasive treatment method must be repeated, and with it comes a large physical toll upon the patient. For example, each time the treatment method is performed, a portion of the patient's bone structure is shaved away.

The diagnostic methods of the present invention may be utilized after spacer implantation and/or prior to re-implantation in order to determine whether or not re-implantation is appropriate. If a serum sample taken from a patient prior to re-implantation has D-dimer levels that are within the normal range (as defined herein), i.e. are not elevated, PJI can be ruled out as a potential pathology with certainty, and the re-implantation can proceed. Thus in some embodiments, the present invention provides for a method of eliminating PJI as a potential pathology, wherein normal D-dimer levels rule out PJI as a potential pathology.

In other embodiments, the present invention provides a method for evaluating whether to proceed with re-implantation, wherein normal D-dimer levels rule out PJI as a potential pathology and thus indicating to proceed with re-implantation, and wherein elevated D-dimer levels indicate the subject as having or at risk of having PJI as a potential pathology and thus indicating to not proceed with re-implantation. In another embodiment, the results of the assay provide a patient specific biomarker profile that is useful to diagnose and detect the risk of developing PJI and optimize a treatment regimen for that patient to maximize clinical outcome.

In some embodiments, the invention is directed to a method for diagnosing a patient who has a surgical implant as having PJI. In another embodiment, the invention is directed to methods of detecting biomarkers associated with PJI. In some embodiments, the method provides for steps of (a) obtaining a serum sample comprising D-dimer from the patient;(b) quantifying the level of D-dimer present in the sample; and (c) diagnosing the patient as having PJI, wherein a D-dimer level greater than 400, 800, 850, 1100, 1200, 1250 ng/mL in the sample indicates the patient as having PJI. In one embodiment, a D-dimer level greater than 850 ng/mL in patients post bone repair or replacement surgery indicates the patient is diagnosed with an infection. In further embodiments, the quantifying step is performed by an immunoassay. In yet further embodiments the serum sample is one of a plasma sample, blood sample, sputum sample, lavage, synovial fluid, or combinations thereof.

5. In some embodiments, the invention is directed to a method for determining whether or not a patient who has undergone spacer insertion should undergo re-implantation. In some embodiments, the method provides for steps of (a) obtaining a serum sample comprising D-dimer from the patient; (b) quantifying the level of D-dimer present in the sample; and (c) determining whether or not to proceed with re-implantation, wherein a D-dimer level greater than 850 ng/mL in the sample indicates to not proceed with re-implantation, and a D-dimer level lower than 850 ng/mL in the sample indicates to proceed with re-implantation.

In yet other embodiments, a D-dimer level greater than 200 ng/mL in the sample indicates to not proceed with re-implantation, and a D-dimer level lower than 200 ng/mL in the sample indicates to proceed with re-implantation.

Those of ordinary skill in the art would appreciate that at least another aspect of the present invention is directed to methods of treating a patient having undergone an orthopedic surgery such as TJA, including the step of first quantifying the D-dimer levels by preferably performing an immunoassay and then treating the patient. In one embodiment the treatment of such patient include performing an orthopedic surgery or repeat the same, at the site that has already undergone the treatment. In further embodiments, the treatment of such patient may include pharmacological modalities such as a regimen of antibiotic therapy including antibiotic containing cements for local administration, wherein the antibiotic includes aminoglycosides, vancomycin, or alike. In yet further embodiments, the sample is one of a serum sample such as plasma sample, blood sample or otherwise sputum sample, lavage, synovial fluid, or combinations thereof.

The methods of detecting and/or quantifying D-dimer levels may be performed according to those methods described herein, or any other methods that are known in the art. In at least one embodiment, the methods for detecting and/or quantifying D-dimer levels may generally be performed according to the following steps. Initially serum samples containing D-dimer are taken from a patient, e.g. a plasma serum sample, although the serum sample is not limited as such. The samples are then subject to an immunoassay that contains antibodies specific for the cross-linked D-dimer domain in fibrinogen. This ensures that the assays are specific for fibrinolysis, as opposed to fibrinogenolysis. These assays may include, for example, ELISA and immunoturbidimetry.

ELISA assays are one potential choice for D-dimer quantitation and are typically most common. ELISA assays utilize microtiter wells (e.g. 96-wells) coated with an antibody, e.g. a monoclonal antibody (mAb) specific for a first epitope on cross-linked D-dimer domain. Incubation with the serum sample results in the binding of the antibody any D-dimer present. A labeled antibody specific for a second epitope on cross-linked D-dimer is then added and the amount of bound labeled substance is determined, for example, by a colorimetric reaction.

Immunoturbidometric assays are microparticle assays in which a beam of light, e.g. monochromatic light, is passed through a suspension of latex microparticles which are bound to antibodies, e.g. monoclonal antibodies, specific for D-dimer. The wavelength of the light, for example but not necessarily 540 nm, is greater than the diameter of the latex microparticles. Therefore, the solution of latex microparticles does not absorbs the light. When the serum sample is added to the suspension, D-dimer present in the sample causes the latex microparticles to agglutinate. The D-dimers aggregate with diameters greater than the wavelength of the light. This increases the absorbance of the light (measured photometrically), and is proportional to the amount of D-dimer present in the test sample.

Other potential assays include whole blood assay for D-dimer utilizing an antibody, e.g. a bispecific antibody specific for D-dimer and a red blood cell antigen. In such assays, typically a drop of whole blood is incubated with the bispecific antibody solution, and if D-dimer levels are elevated, agglutination of blood is observed.

In another aspect of the present invention, diagnostic kits are described that contain assays, microarrays or other qualifying immunoassay components to measure and detect secondary biomarkers such as interlukin-6 (IL-6), IL-10, IL-8, IFN-α, leukocyte level, VEGF, Procalcitonin (PCT), Serum amyloid A (SAA), Mannan (M) and antimannan (AM) antibodies, C-reactive protein (CRP), Toll-like receptor 2 (TLR-2) and neutrophil CD64 receptor (nCD64), and IFN-γ-inducible protein 10 (IP-10) to enhance the sensitivity of the PJI test. In yet another embodiment, the kit may contain components to allow measurements of alpha defensing or employ leukocyte esterase test.

In one embodiment, the present invention provides a method of identifying and treating a subject at risk for developing PJI comprising obtaining a biological sample from the subject, performing an assay to determine the presence or absence of D-dimer, and identifying the subject as at risk for developing PJI or suffering from PJI, if the D-dimer level is higher than 300, 400, 800, 850 or 1100 ng/ml. In another embodiment, a customized treatment plan including antibiotic regimens may be instituted prophylactically to minimize the risk of failure. In another embodiment, the kit can provide a treatment regimen, if at least two, three, or four of said biomarkers in said biological sample are detected. In at least one embodiment, a package labeling may contain instruction of use. In another embodiment, the labeling provides an interpretation of the structural information provided upon the proper use of the assay components of the kit. A kit according to the present invention contains (a) detection reagents which are specific for detection of D-dimer, and optionally second biomarker, wherein said reagents are adapted to detect a threshold level of D-dimer in the blood to indicate a presence of joint infection; and (b) instructions for using said detection reagents to evaluate joint infection in the patient.

In another aspect of the present invention, methods of treatments of patients at risk of PJI are contemplated wherein D-dimer levels provide guidance as to the therapeutic approach towards patients at risk of PJI. In one embodiment, treatment methods may include robust drug treatment to eliminate infection. In another embodiment, methods of treatment may include surgical repair of the regions at risk or re-implantation of an implant.

In other embodiments, D-dimer provides more accuracy compared to the currently available laboratory tests for diagnosing PJI. Thus, those of ordinary skill in the art can appreciate that with better performance, D-dimer can prevent unnecessary revision total joint arthroplasties in patients with suspected PJI. Moreover, D-dimer can detect infection with not only a very high sensitivity, preferably above 80% but also high specificity. This allows timely revision surgery and can potentially limit complications.

D-dimer is a unique tool for detecting the reimplantation time in patients who are going through their second stage revision (reimplantation). Detecting infection eradication plays a very important role in reimplantation patients. If reimplantation is performed in a setting that infection is still persisted, which is not uncommon, it can lead to an early failure requiring redoing a two stage of revision surgery. The main reason for this complication is that the currently available tests are incompetent to determine whether infection is eradicated. D-dimer can eliminate this complication by determining infection eradication very accurately, potentially saving patients for going through multiple revision surgeries.

VII. EXAMPLES

A. Example 1

1. Overview

A prospective study was conducted to investigate the preoperative D-dimer (ng/mL), erythrocyte sedimentation (ESR) (mm/hr), and serum C-reactive protein (CRP) (mg/dL) levels of consecutive primary and revision total joint arthroplasties at hospital institution. PJI was defined using the Musculoskeletal Infection Society criteria. Patients with active ulcer, history of recent trauma (within two weeks), dislocations, and hyper-coagulation disorders were excluded. This cohort includes 21 primary and 21 revision arthroplasties of which 13 were for aseptic failures and 8 had PJI. There were two patients who were undergoing re-implantation after a prior resection arthroplasty.

2. Results

The mean D-dimer level was significantly higher in PJI patients (1262.94 ng/mL±623.3) compared to primary (212.54 ng/mL±90.8) and aseptic revisions (326.54 ng/mL±170.7). D-dimer levels in the patients who were undergoing re-Implantation were also low at 403.54 ng/mL±196.9. When 800 ng/mL was assumed as the threshold level for PJI, all aseptic patients were below the cut-off and septic patients were above it. The mean CRP level was higher in PJI patients (7.0 mg/dL±6.5) compared to primary (0.43 mg/dL±0.4) and aseptic revisions (0.4 mg/dL±0.3). ESR levels followed the same pattern but did not reach statistical significance, 56.1 mm/hr±30.3 in PJI patients compared to 15 mm/hr 9.8 and 17.7 mm/hr±10.4 in primary and aseptic revisions, respectively ($P>0.05$).

B. Example 2

2. Patient Demographics

Upon institutional review board approval patients who underwent total joint arthroplasty (TJA) were enrolled in the study. The included patients were divided into four groups depending on the procedure; primary TJA (group A), revision due to aseptic reasons (group B), spacer insertion (group C), and re-implantation (group D). All patients had undergone primary and revision total knee and hip arthroplasties. Patients were excluded with history of VTE/PE, cancer, those with an active ulcer, and those who were early post-operative period (30 days). Serum D-dimer, erythrocyte sedimentation rate (ESR), and C-reactive protein (CRP) were measured from the sample that was obtained before the surgery in the operating room holding area. Total patient number ended up being 82 patients; 22 patients in group A; 26 patients in group B; 27 patients in group C, and 20 patients in group D. The demographics of the patient group are presented below in

TABLE 1

Demographic information of the enrolled patients.

| Patients | Gender | Age (years) | BMI (kg/m$^2$) |
|---|---|---|---|
| Group A (N = 22) Primary TJA | (12 male, 10 female) | 64.5 (35-91) | 32.7 ± 5.3 |
| Group B (N = 26) Aseptic Revision | (12 male, 14 female) | 63.3 (43-78) | 33.2 ± 6.4 |
| Group C (N = 27) Septic Revision (spacer insertion) | (14 male, 13 female) | 67.2 (38-81) | 34.1 ± 6.2 |

TABLE 1-continued

Demographic information of the enrolled patients.

| Patients | Gender | Age (years) | BMI (kg/m²) |
|---|---|---|---|
| Group D (N = 20) Re-implantation | (9 male, 11 female) | 65.8 (36-81) | 30.3 ± 3.5 |

2. Results

Figure 2:
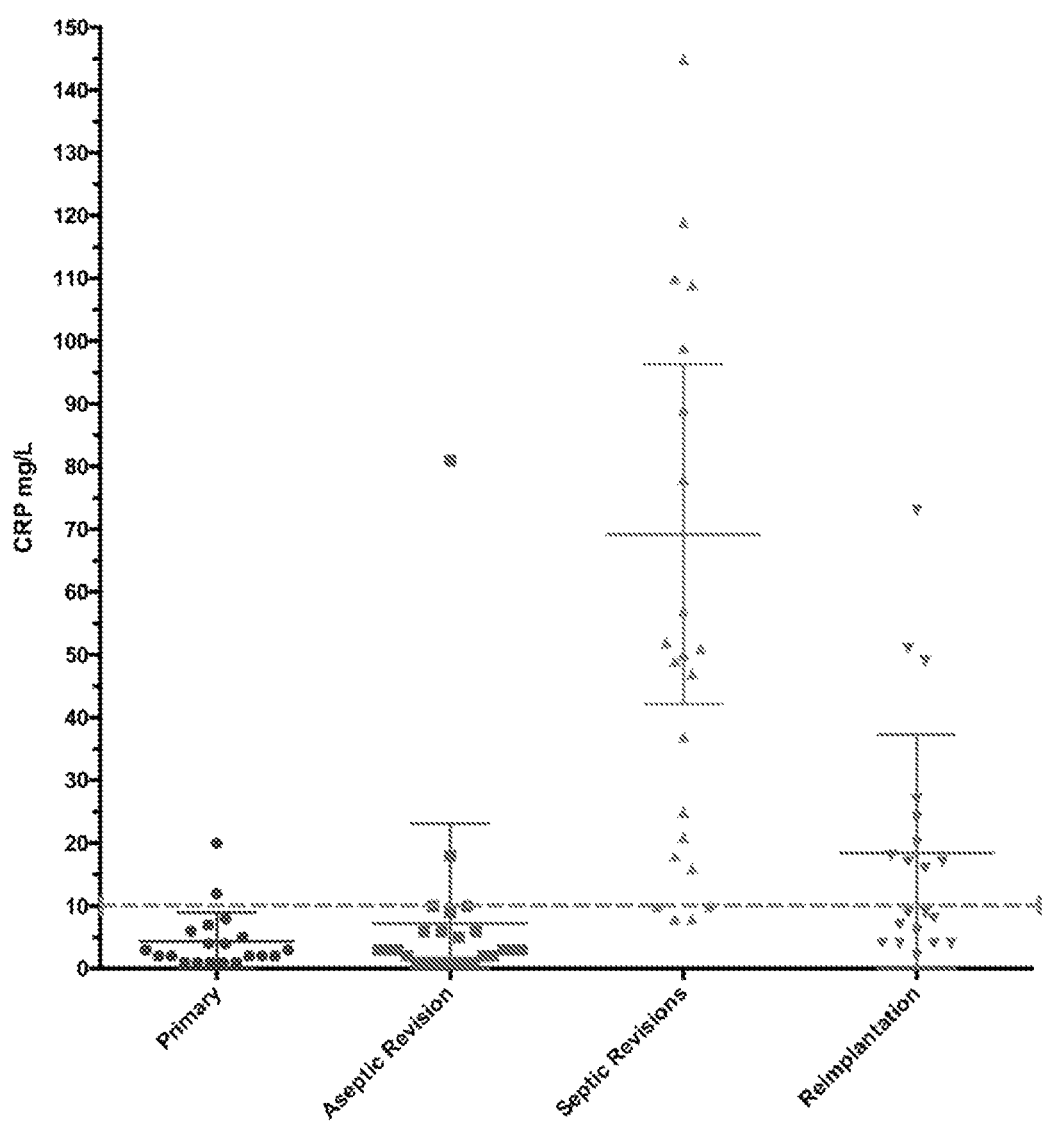
FIG. 2 displays C-reactive protein (CRP) levels in the patient study groups of Example 2.
Figure 3:
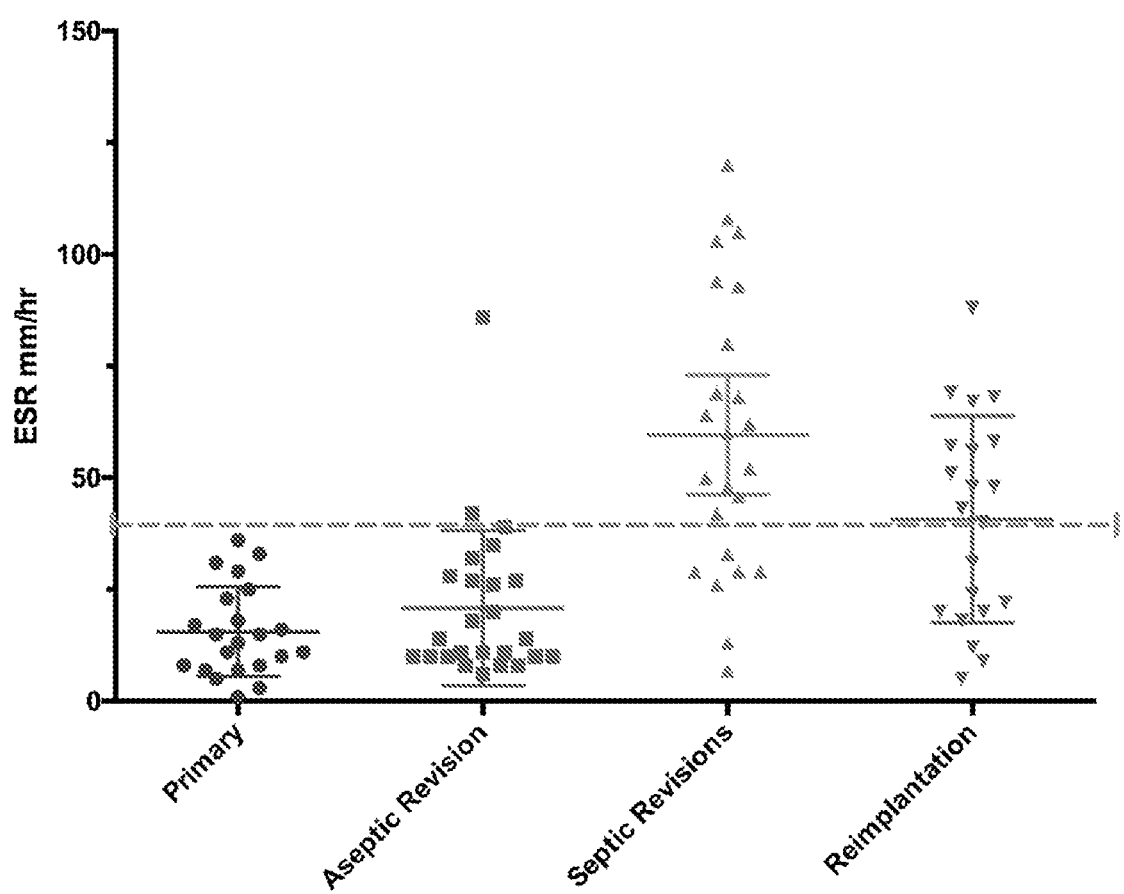
FIG. 3 displays Erythrocyte sedimentation rate (ESR) is in the patient study groups of Example 2.

Descriptive statistics were used to report all laboratory values. One-way analysis of variance (ANOVA) and Youden's J statistic were used to compare the means. A p-value of <0.05 was considered statistically significant. Serum D-dimer was significantly higher in patients with PJI (p-value<0.05). The mean D-dimer in primary patients (group A) was 212.5 ng/mL; this value was 347 ng/mL in aseptic revisions (group B). In septic revisions patients (group C) the D-dimer level was significantly higher compared to all the other groups: 1384.8 ng/mL (p-value<0.0001). Surprisingly and unexpectedly, in the re-implantation group (group D) the D-dimer level reduced back to below 500 ng/ml, 403.5 ng/mL [FIG. 1]. The CRP level was 4.35 mg/dL in primary cases (group A), 7.28 mg/dL in aseptic revisions (group B), and 69.25 mg/dL, in septic cases (group C), and 18.45 mg/dL±1.2 in reimplantations (group D) [FIG. 2]. The ESR level followed the same pattern. The ESR was 15 mm/hr in primaries (group A), 20.84 mm/hr in aseptic revisions (group B), 50.5 mm/hr in spacer insertion (p-value<0.0001) (group C), and 40.6 mm/hr in re-implantations (group D) [FIG. 3]. These results are summarized below in Table 2. Sensitivity of the D-dimer test was 100%, whereas sensitivity for ESR was 78% and CRP was 74%. The lower limit for the D-dimer was 84% with an upper limit of 100%, for ESR was 53% lower limit with an upper limit of 88%, and for CRP was a lower limit of 52% and an upper limit of 88%. Thus, the D-dimer test showed much greater sensitivity than both ESR and CRP level measurement.

TABLE 2

Summarized results from Example 2

| Patients | D-dimer Level (ng/mL) | CRP Level (mg/dL) | ESR (mm/hr) |
|---|---|---|---|
| Group A (N = 22) Primary TJA | 212.5 (150-430) | 4.35 (1-20) | 15.5 (5-36) |
| Group B (N = 26) Aseptic Revision | 347 (150-1114) | 7.28 (1-81) | 20.84 (6-86) |
| Group C (N = 27) Septic Revision (spacer insertion) | 1384.8 (806-3457) | 59.5 (7-120) | 59.5 (7-120) |
| Group D (N = 20) Re-implantation | 430.9 (110-640) | 18.45 (2-73) | 40.6 (5-88) |

C. Example 3

Similar study as in Example 2 were further expanded into a larger population.

1. Materials and Methods:

Upon institutional review board approval, patients who underwent total joint arthroplasty (TJA) were enrolled in this prospective study. Patients undergoing primary and revision arthroplasties were included except those with any type of skin ulcer, hematoma, recent trauma or dislocation (within two weeks), visible ecchymosis, prosthetic heart valves, and those with hypercoagulation disorders.

The patients enrolled in this study fall under five categories: those undergoing primary total joint arthroplasty (group A), revision arthroplasty due to aseptic failure (group B), patients undergoing resection arthroplasty and spacer insertion for the treatment of PJI (group C), and patients with treated PJI undergoing reimplantation surgery (reimplantation) (group D), and finally patients with known infection in a site other than a joint (group E).

Sex, age, joint, comorbid conditions including systemic inflammatory disease such as rheumatoid arthritis, lupus erythrematosus, psoriasis, polymyalgia rheumatica, and sarcoidosis, and history of inflammatory bowl disease, gout, hepatitis B and C, lymphocytic leukemia, myelodysplastic syndrome, and multiple myeloma, concurrent antibiotic treatment (not including a single dose of prophylactic perioperative antibiotic), and isolated organisms were recorded. A venous blood sample was obtained right before surgery and analyzed for serum D-dimer, erythrocyte sedimentation rate (ESR), and C-reactive protein (CRP). PJI was defined using the MSIS criteria. As part of the standard protocol at the hospital institution, surgeons obtain multiple intraoperative tissue culture specimens from patients undergoing revision arthroplasty. The cultures are usually incubated for up to fourteen days. Furthermore, when a pre-operative synovial fluid aspiration is performed, cultures are requested.

The cohort consists of 245 patients; primary arthroplasty (N=23), aseptic revisions (N=86), revisions for PJI (N=57), reimplantations (N=29), and those with infection in areas other than a joint (N=50), that included 34 cases of urinary tract infections, 9 cases of pneumonia, and 5 cases of upper respiratory infections. (Table 3). Patients were followed closely, the nature of complications and reason for readmission or reoperation were recorded.

TABLE 3

Number of patients in each study group and the corresponding serum biomarker results.

| Patients | D-dimer Level (ng/mL) | CRP Level (mg/dL) | ESR (mm/hr) |
|---|---|---|---|
| Group A (N = 23) Primary TJA | 1100 (243-8,487) | 56 (2-328) | 46 (5-36) |
| Group B (N = 86) Aseptic Revision | 299 (106-6,381) | 8.2 (1-81) | 15.3 (1-36) |
| Group C (N = 57) Septic Revision (spacer insertion) | 1384.8 (806-3457) | 59.5 (7-120) | 59.5 (7-120) |
| Group D (N = 29) Re-implantation | 430.9 (110-640) | 9.2 (1-27) | 75.2 (7-121) |
| Group E (N = 50) Other infections | 451 (150-1420) | 47 (1-179) | 72 (35-121) |

2. Statistical Analysis

Descriptive statistics were used to report all the laboratory values. The results of the diagnostic tests were compared between the groups using Mann-Whitney test considering a p-value<0.005 as a significance of difference between the groups. The cutoff of 850 ng/mL was considered as the PJI diagnostic threshold for the D-dimer test. This optimum cutoff value was determined by Youden's J statistic based on its correspondence with the MSIS-defined diagnosis. The sensitivity and specificity of the diagnostic tests were calculated along with their 95% confidence intervals. All the statistical analyses were performed using GraphPad Prism, version 7.0a, GraphPad software Inc. California, USA.

Figure 4:
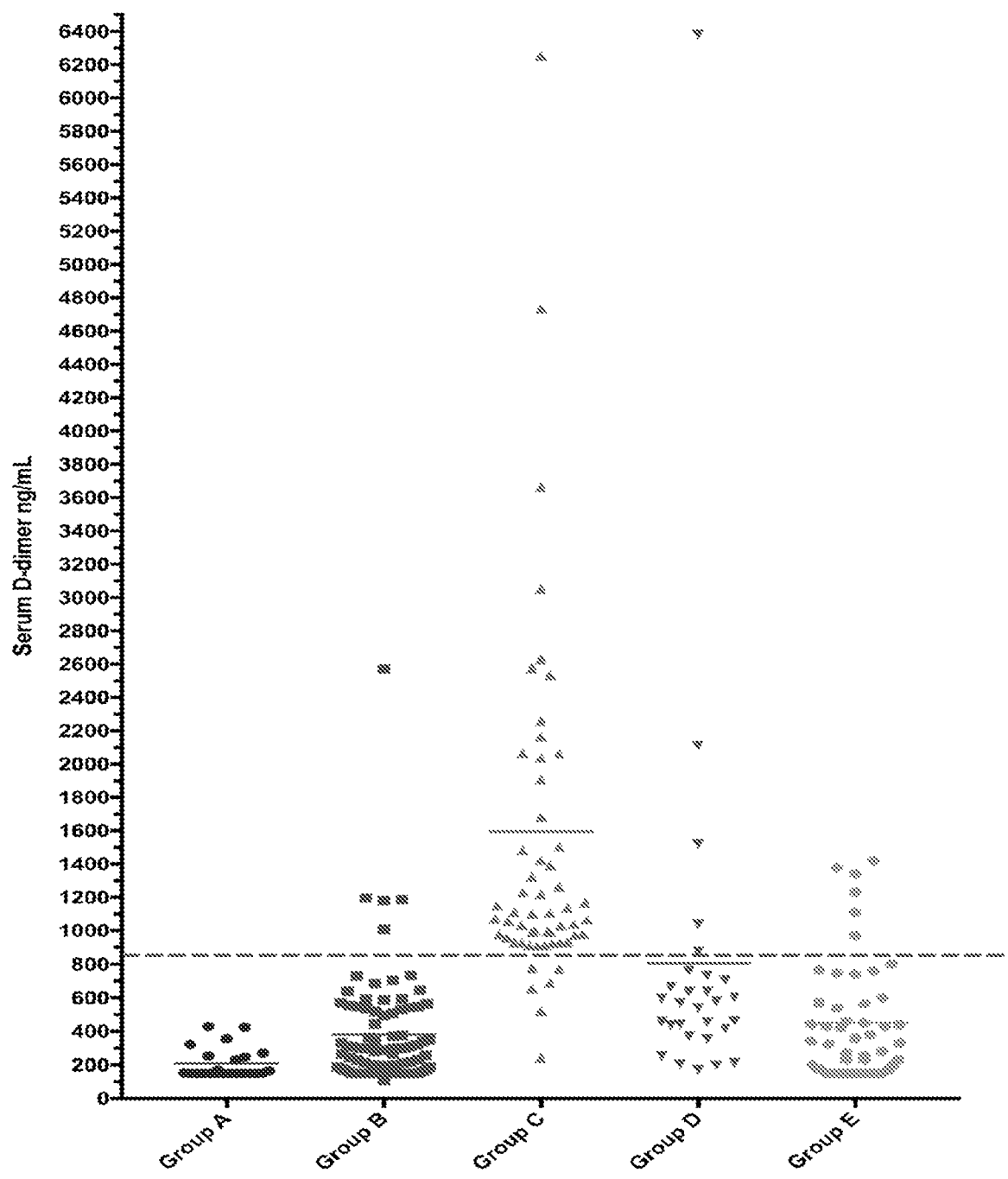
FIG. 4 displays D-dimer levels in the study groups. The dashed horizontal line determines the calculated threshold for diagnosis of PJI. (850 ng/mL)

3. Results:

Serum D-dimer was significantly higher in patients with PJI; median of D-dimer was 1,110 ng/mL in the PJI group versus 299 ng/mL in cases that were not infected (p-value<0.0001). The mean D-dimer was 212.5 ng/mL (range: 150-430 ng/mL) in the primary arthroplasty cohort, 399.9 ng/mL (range: 106-2,571 ng/mL) in the aseptic revision arthroplasty cohort, 1, 634 ng/mL (range: 243-8,487 ng/mL) in PJI patients (patients who underwent revision arthroplasty due to infection), 806.7 ng/mL (range: 170-6, 381 ng/mL) in the reimplantation group, and 451 ng/mL (range: 150-1,420 ng/mL) in patients with infection in sites other than a joint (FIG. 4).

Figure 5:
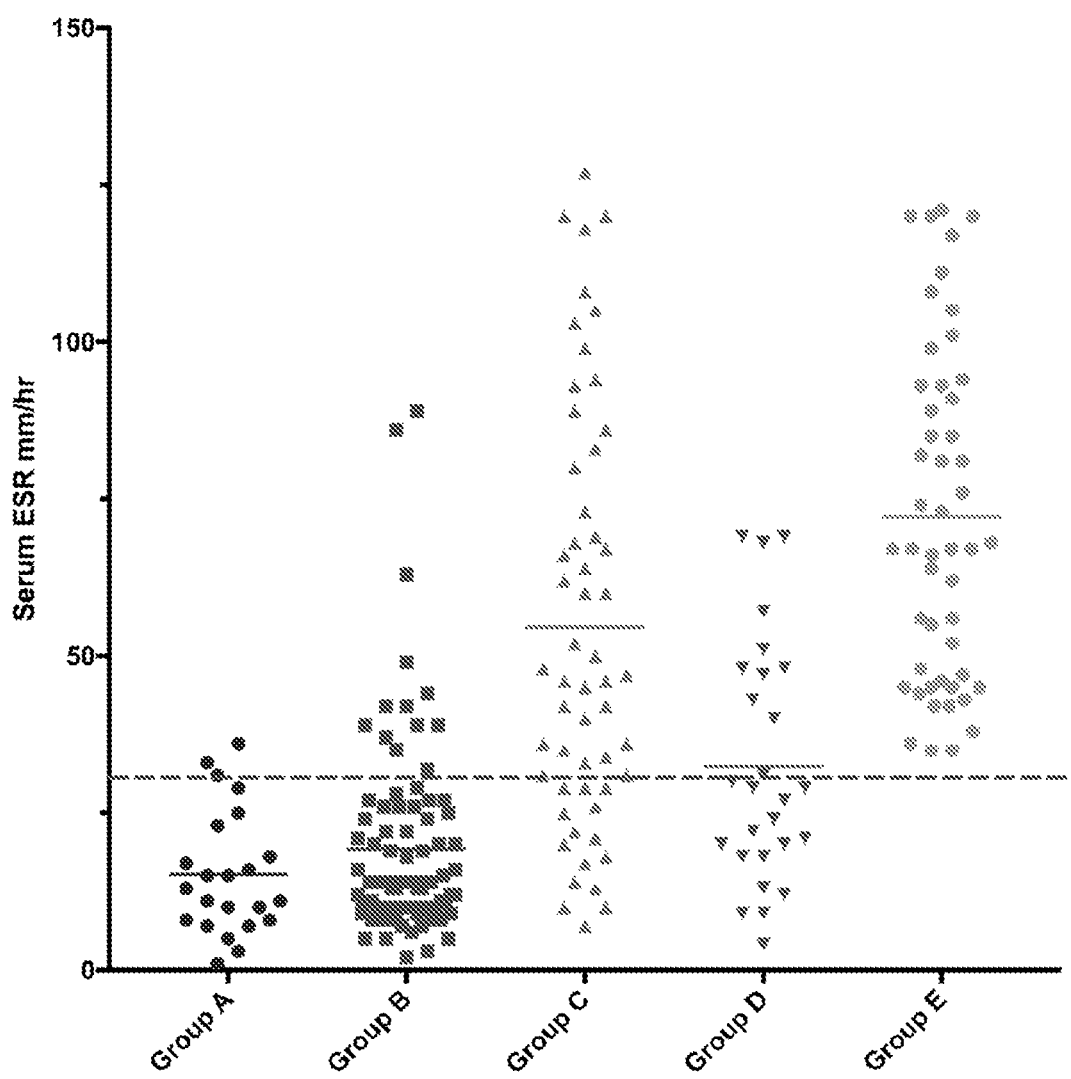
FIG. 5 displays ESR levels in the study groups. The dashed horizontal line determines the threshold recommended by the musculoskeletal infection society (30 mm/hr)
Figure 6:
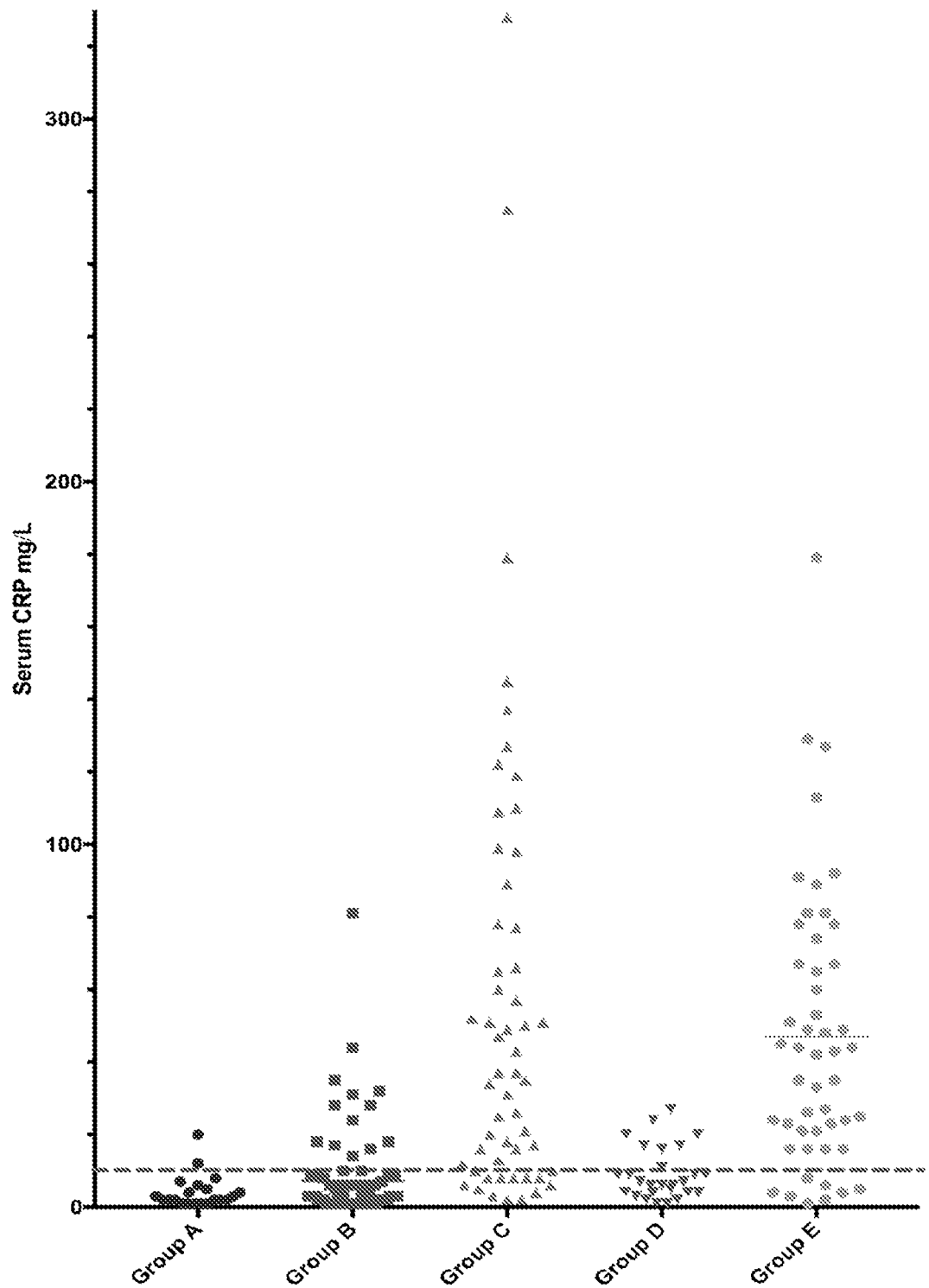
FIG. 6 displays CRP levels in the study groups of Example 3. The dashed horizontal line determines the threshold recommended by the musculoskeletal infection society (10 mg/L). Group A: Primary arthroplasties, Group B: Aseptic revisions, Group C: Revisions for infection, Group D: Reimplantations, and Group E: Patients with infection in sites other than a joint.

The median ESR and CRP were also significantly higher in patients with PJI; the median of ESR was 46 mm/hr (range, 7 to 127 mm/hr) in PJI patients compared to 15 mm/hr (range, 1 to 89 mm/hr) in the non-infected cohort (p<0.0001) and for CRP the median was 37 mg/L (range, 2 to 328 mg/L) in the PJI group vs. 3 mg/L (range, 1 to 81 mg/L) in the non-infected cases (p<0.0001). The mean ESR was 15.3 mm/hr (1-36 mm/hr) in the primary arthroplasty cohort, 19.2 mm/hr (2-89 mm/hr) in the aseptic revision arthroplasty cohort, 75.2 mm/hr (7-120 mm/hr) in PJI patients (patients who underwent revision arthroplasty due to infection), 32.4 mm/hr (4-69 mm/hr) in the reimplantation group, and 72 (35-121 mm/hr) in patients with infection in sites other than a joint (FIG. 5). The mean CRP was 4.2 mg/L (1-20 mg/L) in the primary group, 8.2 mg/L (1-81 mg/L) in aseptic revisions, 56 mg/L (2-328 mg/L) in PJI patients, 9.2 mg/L (1-27 mg/L) in the reimplantation group, and 47 mg/L (1-179 mg/L) in patients with infection in sites other than a joint (FIG. 6). Serum CRP and ESR had a sensitivity of 78% (95% Confidence interval [CI]: 66-88%) and 73% (95% CI: 60-84%) and a specificity of 80% (95% CI: 72-86%) and 78% (95% CI: 70-85%) respectively.

The sensitivity and specificity of ESR and CRP combined was 84% (95% CI: 76-90%) and 47% (95% CI: 36-58%), respectively. Serum D-dimer test had a better sensitivity at 89% (95% CI: 77-95%) and a better specificity at 92% (95% CI: 86-96%) for diagnosing PJI. D-dimer played an excellent role in predicting the presence of infection at the time of reimplantation. Five patients had elevated D-dimer at the time of reimplantation. Of these two patients who were reimplanted also had a positive culture (*Propionibacterium acnes* in one and *Staphylococcus epidermidis* in the other one). Both of these patients ultimately failed and required treatment for infection. It is interesting to note that the corresponding CRP and ESR levels were falsely negative in both of these patients (CRP: 8 and 1 mg/L and ESR: 20 and 9 mm/hr). The other three patients with "false positive" D-dimer at the time of reimplantation were followed.

The rate of culture negative PJI in the cohort was 33% (19/57). The false negative rate for D-dimer in this subgroup was 5% (1/19) whereas it was 47% (9/19) for CRP and 52% (10/19) for ESR (Table 3). The data related to patients with infection in sites other than a joint was very interesting. All 50 patients (100%) had elevated ESR (>30 mm/hr), 42 patients (84%) had elevated CRP (>10 mg/L), and the D-dimer was elevated above 850 ng/dL in 6 patients (12%). D-dimer for diagnosis of PJI appears to be a better test than ESR and CRP even in patients with inflammation or infection in non-joint sites.

Discussion

This is, to inventor's knowledge, the first study that evaluates the role of serum D-dimer as a diagnostic test for PJI and predicting the presence of infection in patients awaiting reimplantation. In the given cohort, which we assembled over the past two years, D-dimer had a better "performance" than ESR and CRP, even when combined. These results demonstrate that patients with PJI have a significantly and consistently higher levels of serum D-dimer. The D-dimer was particularly impressive in the setting of reimplantation.

Out of five patients with "elevated" D-dimer at the time of reimplantation, two patients had a positive culture from the samples taken during reimplantation, who subsequently failed. ESR and CRP were both normal in these two patients. Both of these two patients have subsequently failed as a result of infection. Thus, it is believed that the sensitivity and the specificity of D-dimer is likely higher than calculated in this cohort as some of the patients with "positive" D-dimer who were classified as non-infected, may indeed have infection by slow growing organisms that did not elicit physiological inflammation and failed to meet the MSIS criteria for PJI. The MSIS workgroup proposing the PJI definition cautioned the clinicians about such possibility, when organisms like *P. acne* causing PJI may not elicit adequate inflammation and all minor criteria may be negative. Thus, using the MSIS criteria for those patients may have adversely affected the performance of D-dimer.

Clinicians are familiar with serum D-dimer as it has been used, albeit with disappointing performance, for screening of patients for venous thromboembolism (VTE). However, in the present case, those of ordinary skill in the art can appreciate that increased fibrinolytic activity and generation of byproducts such as D-dimer may attribute to localization of the infecting organisms or inflammatory cells and preventing their systemic damage. As shown herein the inventors has shown that the byproduct of the fibrinolytic activity also "leaks" into the circulation and can thus be measured as a surrogate for local infection at the arthroplastic site. D-dimer is a byproduct of cross-linked fibrin degradation and is present in the serum of most healthy individuals but only in negligible amounts (approximately 100-200 ng/mL).

Those of ordinary skill in the art can appreciate that at least one strength of this study among other things can be attributed to the fact that patients were recruited prospectively and unlike most diagnostic studies that limit their population to patients without concurrent inflammatory conditions, the cohort was heterogeneous and included patients with inflammatory conditions, metallosis, wear, as well as those who were receiving ongoing antibiotic therapy. The inclusion of these patients provided a more realistic clinical situation allowing for the evaluation of D-dimer in a real world practice. As part of the ongoing efforts, numerous other serum biomarkers were investigated in the animal model of PJI and also in a small cohort of patients and found that D-dimer outperformed all of the other serum markers of infection.

The second strength of this study is that it included a cohort of "positive control" patients with infection at sites other than a joint. This allowed us to evaluate the "false positive" rate for D-dimer if it were to be used for diagnosis of PJI. It certainly appeared that D-dimer is a better test than ESR and CRP in this clinical setting as it was elevated in only 12% of patients compared to ESR being elevated in 100% and CRP being elevated in 84% of patients.

The other strength of this study is that it evaluated the role of a serum marker for patients undergoing reimplantation, arguably the most understudied area in orthopedic infections. D-dimer appeared to have an impressive performance in that setting also. Finally, the statistical methods used here is to determine the appropriate threshold for D-dimer for diagnosis of PJI. Although the latter could change with addition of further data from an institution stand point, it is a great starting point and a guide to clinicians who may wish to use this test.

As there is no "gold standard" for diagnosis of PJI, some of the patients that were allocated in the non-infection group might be in fact infected. The MSIS criteria for PJI even though accepted as the best definition of PJI may be supplemented as provided by the instant data. Although patients with systemic inflammatory diseases and those who received immunosuppressive therapies were not excluded from this study, the cohort contains a few patients with these conditions.

This prospective study on a large cohort of patients demonstrates, for the first time, the real value of serum D-dimer for diagnosis of PJI and in determining the presence of infection in patients undergoing reimplantation. Based on the findings of this study, it is believed that serum D-dimer, an inexpensive and universally available test, should be added to the work-up of patients for PJI. Elevated D-dimer for patients undergoing reimplantation should be taken seriously as it could be an indication of presence of infection in that setting.

Equivalents

One of ordinary skill in the art will recognize that there are many equivalents of the specific embodiments disclosed herein, and that those equivalents will require no more than routine experimentation in the art. Therefore, those equivalents must be considered part of this invention and as such must be considered to be covered by the following claims.

All references and citations disclosed herein are to be considered incorporated by reference in their entirety.

What is claimed is:

1. A method of treating a patient with a surgical implant for a periprosthetic joint infection (PJI), the method comprising:
   (a) obtaining a serum sample comprising D-dimer from the patient;
   (b) quantifying the level of D-dimer present in the serum sample; and
   (c) administering at least one antibiotic to the patient to treat the periprosthetic joint infection, or surgically repairing the infected region, when the D-dimer level in the serum sample is greater than 850 ng/mL.

2. The method of claim 1, wherein the quantifying step is performed by an immunoassay.

3. The method of claim 1, wherein the serum sample is at least one selected from the group consisting of a plasma sample, blood sample, sputum sample, lavage, synovial fluid, and any combinations thereof.

4. A method of screening a patient for treating a patient in need of re-implantation of an implant, the method comprising:
   (a) obtaining a serum sample comprising D-dimer from the patient;
   (b) quantifying the level of D-dimer present in the serum sample; and
   (c) performing re-implantation of the implant when the D-dimer level is lower than 850 ng/mL in the serum sample.

5. The method of claim 4, wherein the quantifying step is performed by an immunoassay.

6. The method of claim 4, wherein the serum sample is at least one selected from the group consisting of a plasma sample, blood sample, sputum sample, lavage, synovial fluid, and any combinations thereof.

7. The method of claim 1, wherein the at least one antibiotic is selected from the group consisting of aminoglycosides and vancomycin.

8. A method of treating a patient at a risk of developing periprosthetic joint infection (PJI), the method comprising:
   (a) obtaining a serum sample comprising D-dimer from the patient;
   (b) quantifying the level of D-dimer present in the serum sample; and
   (c) surgically repairing the infected region when the D-dimer level in the serum sample is greater than 850 ng/mL.

9. The method of claim 8, wherein step (b) further comprises quantifying the level of at least two secondary biomarkers selected from the group consisting of interleukin-6 (IL-6), IL-10, IL-8, IFN-α, leukocyte, VEGF, Procalcitonin (PCT), Serum amyloid A (SAA), Mannan (M) and antimannan (AM) antibodies, C— reactive protein (CRP), Toll-like receptor 2 (TLR-2), neutrophil CD64 receptor (nCD64), and IFN-γ-inducible protein 10 (IP-10).

10. The method of claim 8, wherein the serum sample is at least one selected from the group consisting of a plasma sample, blood sample, sputum sample, lavage, synovial fluid, and any combinations thereof.

11. The method of claim 8, wherein the serum sample is obtained preoperatively or intraoperatively.

* * * * *